(12) United States Patent
Wang et al.

(10) Patent No.: US 7,964,072 B2
(45) Date of Patent: Jun. 21, 2011

(54) SENSOR MATERIAL AND GAS SENSOR ELEMENT AND GAS SENSOR DERIVED THEREFROM

(75) Inventors: Da Yu Wang, Troy, MI (US); Sheng Yao, Macomb, MI (US); Thomas M. Brunette, Flushing, MI (US); Elizabeth Briggs, Chesterfield Township, MI (US); Raymond L. Bloink, Swartz Creek, MI (US); David D. Cabush, Howell, MI (US)

(73) Assignee: Delphi Technologies, Inc., Troy, MI (US)

( * ) Notice: Subject to any disclaimer, the term of this patent is extended or adjusted under 35 U.S.C. 154(b) by 284 days.

(21) Appl. No.: 12/245,248

(22) Filed: Oct. 3, 2008

(65) Prior Publication Data

US 2010/0084269 A1 Apr. 8, 2010

(51) Int. Cl.
*G01N 27/407* (2006.01)
(52) U.S. Cl. ......... 204/424; 205/781; 501/123; 501/126
(58) Field of Classification Search .................. 204/424; 205/781; 501/123, 126
See application file for complete search history.

(56) References Cited

U.S. PATENT DOCUMENTS

| | | | |
|---|---|---|---|
| 4,279,763 A | | 7/1981 | Boeuf et al. |
| 4,462,889 A | * | 7/1984 | Landon et al. ................ 204/292 |
| 4,582,623 A | | 4/1986 | Kubo et al. |
| 4,781,852 A | * | 11/1988 | Kaczur et al. ............... 252/62.59 |
| 4,797,331 A | * | 1/1989 | Watada et al. .............. 428/822.1 |
| 5,846,449 A | * | 12/1998 | Taguchi et al. ............ 252/62.62 |
| 7,294,252 B2 | | 11/2007 | Wang et al. |
| 2007/0080075 A1 | | 4/2007 | Wang et al. |
| 2010/0032292 A1 | * | 2/2010 | Wang et al. ................... 204/431 |

FOREIGN PATENT DOCUMENTS

EP 1365425 11/2003

OTHER PUBLICATIONS

EP Search Report dated Jan. 29, 2010.
Miura N et al: "High-performance solid-electrolyte carbon dioxide sensor with a binary carbonate electrode" Sensors and Actuators B, Elsevier Sequoia S.A., Lausanne, CH, vol. 9, No. 3, Oct. 1, 1992, pp. 165-170, XP026567045 ISSN: 0925-4005 [retrieved on Oct. 1, 1992].

* cited by examiner

*Primary Examiner* — Kaj K Olsen
(74) *Attorney, Agent, or Firm* — Thomas N. Twomey

(57) ABSTRACT

A $NO_X$ sensor material includes a composition of $Ba_{(1-X)}A_XFe_{(12-Y)}B_YO_{19}$. Constituent A and constituent B are doping elements. Constituent A is selected from the group consisting of Bi, La and Pb and X is a real number where $0 \leq X < 1$. Constituent B is selected from the group consisting of Al, B, Bi, Ca, Co, Cr, Cu, Er, Ga, In, Mg, Mn, Ni, Nb, Rh, Pb, Si, Sr, Ti, Ta, Zn and Zr and Y is a real number where $0 \leq Y < 12$. The $NO_X$ sensor material may be used in a sensor element of a $NO_X$ sensor.

25 Claims, 6 Drawing Sheets

SENSOR MATERIAL AND GAS SENSOR ELEMENT AND GAS SENSOR DERIVED THEREFROM

BACKGROUND

Exhaust gas generated by combustion of fossil fuels in furnaces, ovens, and engines contain, for example, nitrogen oxides ($NO_X$), unburned hydrocarbons (HC), and carbon monoxide (CO), which are undesirable pollutants. Vehicles, e.g., diesel vehicles, utilize various pollution-control after treatment devices (such as a $NO_X$-absorber(s) and/or Selective Catalytic Reduction (SCR) catalyst(s)), to reduce $NO_X$. For diesel vehicles using SCR catalysts, $NO_X$ reduction can be accomplished by using ammonia ($NH_3$) gas. However, the presence of $NH_3$ can also interfere with various types of $NO_X$ sensors, thereby reducing their accuracy. In order for SCR catalysts to work efficiently and to avoid pollution breakthroughs, more effective control systems are needed. The development of more effective control systems requires commercial $NO_X$ sensors with the improved accuracy and sensitivity to the various $NO_X$ constituent species with reduced susceptibility to $NH_3$ cross-interference.

For example, existing $NO_X$ sensing materials having the chemical composition of the general form $([A][B])_2O_4$ or $[A][B]O_3$, which include stoichiometric amounts of A, where A is metal elements capable of +3 valence state, and B, where B is Fe or Cr, are sensitive to NO and $NO_2$. They are used as electrode materials in electrochemical devices for $NO_X$ sensing by virtue of the fact that they generate an electromotive force (emf) when exposed to $NO_X$, the magnitude and polarity of which may be characterized using the non-equilibrium Nernst Equation. However, generally, they are sensitive to cross-interference with $NH_3$ which tends to limit their usefulness to applications where $NH_3$ is not a concern. In addition, their $NO_X$ electromotive force (emf) outputs are not large, resulting in non-optimal signal-to-noise ratios. As such, while useful in some applications, these sensors are not generally suitable for applications that require sensors that are insensitive to cross-interference with $NH_3$ or relatively larger $NO_X$ electromotive force (emf) outputs (i.e., improved signal-to-noise performance) or both.

Thus, cost effective $NO_X$ sensors having reduced sensitivity to cross-interference from $NH_3$, or relatively high emf outputs or both, that can reliably sense $NO_X$ under exhaust gas conditions would be desirable for use in various $NO_X$ control systems.

SUMMARY

A $NO_X$ sensor material that may be used to make sensor elements having reduced sensitivity to cross-interference from $NH_3$, or relatively high emf outputs or both, that can reliably sense $NO_X$ under exhaust gas conditions is described herein.

In one aspect, a $NO_X$ sensor material includes a composition of $Ba_{(1-X)}A_XFe_{(12-Y)}B_YO_{19}$. Constituent A and constituent B are doping elements. Constituent A is selected from the group consisting of Bi, La and Pb and X is a real number where $0 \leq X < 1$. Constituent B is selected from the group consisting of Al, B, Bi, Ca, Co, Cr, Cu, Er, Ga, In, Mg, Mn, Ni, Nb, Rh, Si, Sr, Ti, Ta, Zn and Zr and Y is a real number where $0 \leq Y < 12$. The $NO_X$ sensor material may be used in a sensor element of a $NO_X$ sensor.

In another aspect, a $NO_X$ sensor material includes a composition of $Ba_{(1-X)}A_XFe_{(12-Y-Z)}B_YC_ZO_{19}$. Constituent A, constituent B and constituent C are doping elements. Constituent A is selected from the group consisting of Bi, La and Pb and X is a real number where $0 \leq X < 1$. Constituents B and C are selected from the group consisting of Al, B, Bi, Ca, Co, Cr, Cu, Er, Ga, In, Mg, Mn, Ni, Nb, Pb, Si, Rh, Sr, Ti, Ta, Zn and Zr and Y+Z is a real number where $0 \leq Y+Z < 12$.

BRIEF DESCRIPTION OF THE DRAWINGS

Referring now to the drawings wherein like elements are numbered alike in the several figures.

DETAILED DESCRIPTION

The $NO_X$ sensor materials and sensor elements and cells described herein may be employed in various forms of $NO_X$ sensors, or any type of gas sensor element where $NO_X$ sensing can be advantageous. Non-limiting examples of gas sensor elements where $NO_X$ sensing can be advantageous include $O_2$ sensors, $H_2$ sensors, CO sensors, HC sensors, and $NH_3$ sensor elements. A combination comprising at least one of the foregoing can also be used.

Figure 1:
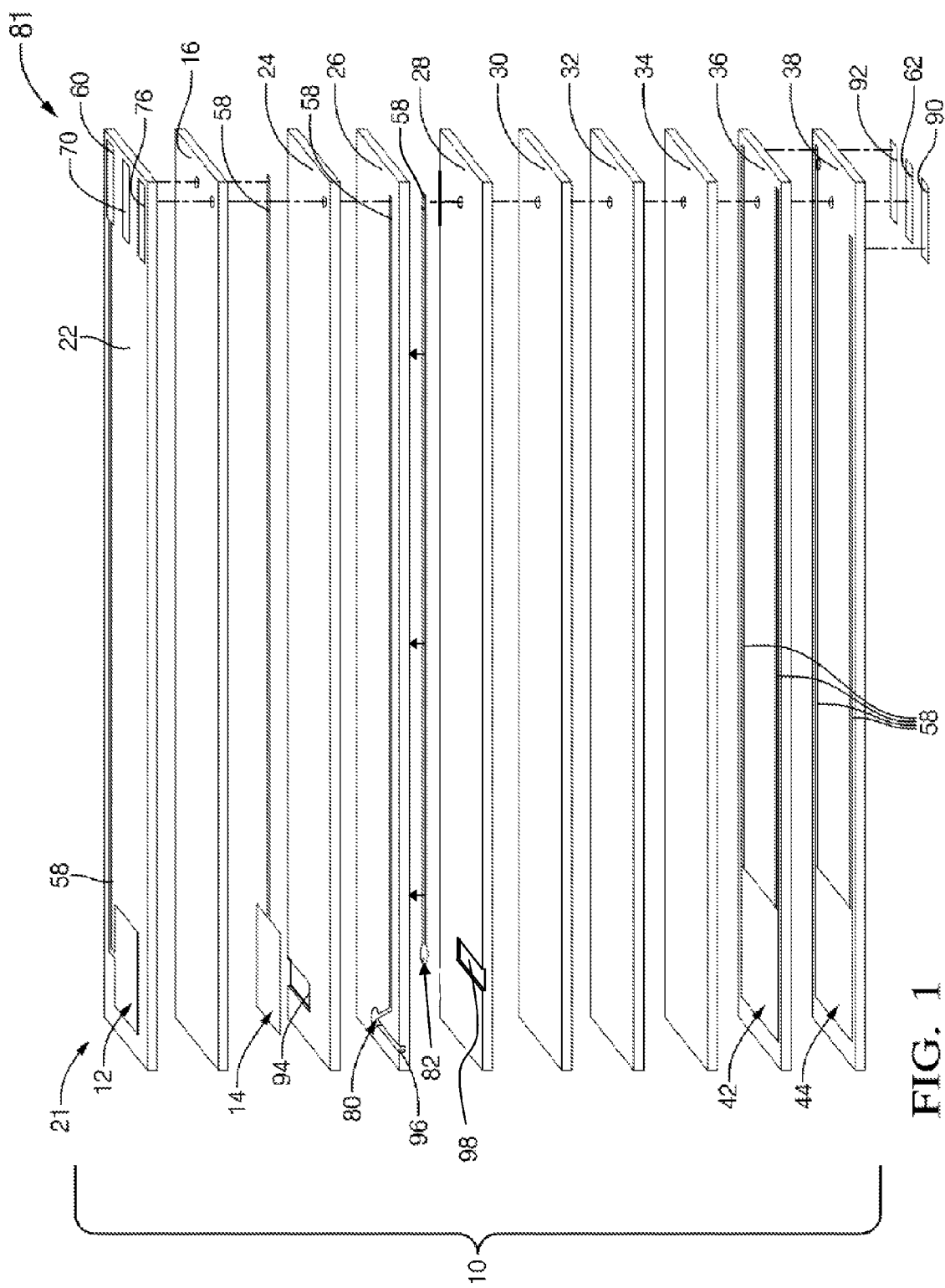
FIG. 1 is an exploded view of an exemplary embodiment of a gas sensor element as described herein.

Referring now to FIG. 1, an exploded view of an exemplary gas sensor element 10 is shown. It is to be understood that although the invention is described in relation to a flat plate sensor, other two and three dimensional sensor designs can also be employed, such as conical, cylindrical, and the like, which also employ the arrangement of the elements described herein in a different physical configuration.

Figure 2:
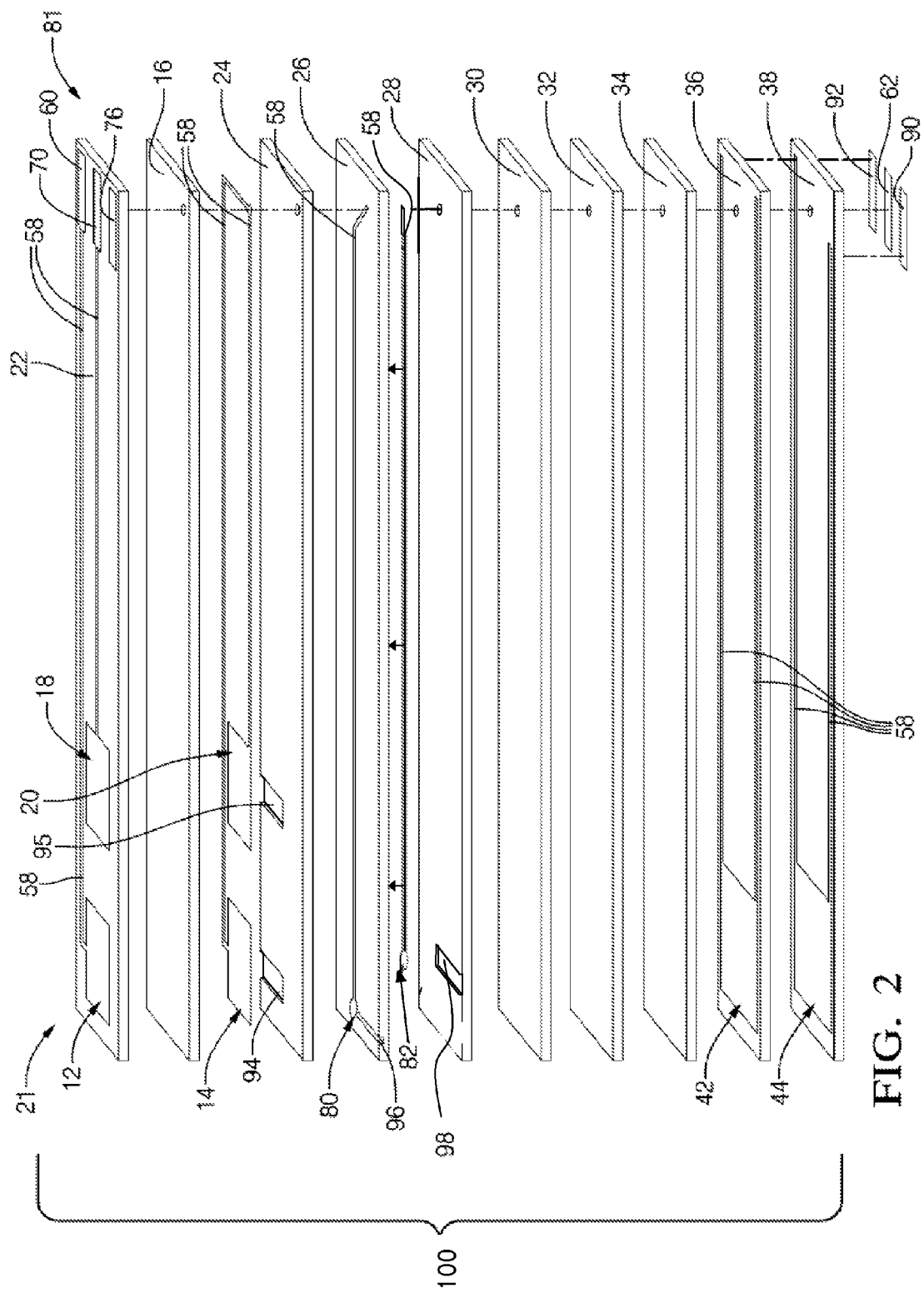
FIG. 2 is an exploded view of an second exemplary embodiment of a gas sensor element as described herein.

Referring to FIGS. 1 and 2, a first exemplary sensing element 10 (as shown in FIG. 1) includes a $NO_X$ sensing cell (12/16/14) including a first sensing electrode 12, a first reference electrode 14 and an electrolyte layer 16, and a second exemplary sensing element 100 (as shown in FIG. 2) includes a second $NO_X$ sensing cell (18/16/20) including a second sensing electrode 18, a second reference electrode 20 and the electrolyte layer 16. The $NO_X$ sensing cells 12/16/14, 18/16/20 are disposed at a sensing end 21 of the sensing element 10. The sensing elements 10,100 include insulating layers 22, 24, 28, 34, 36, 38, and active layers, which include the electrolyte layer 16 and layers 26, 30, and 32. The active layers can conduct oxygen ions, where the insulating layers can insulate sensor components from electrical and ionic conduction. In an exemplary embodiment, the electrolyte layer 16 is disposed between insulating layers 22 and 24, active layer 26 is disposed between insulating layers 24 and 28, and active layers 30 and 32 are disposed between insulating layers 28 and 34.

The sensing elements 10,100 can further include a temperature sensor (not shown), an air-fuel sensing cell comprising the active layer 26 along with an electrode 80 and an electrode 82 (80/26/82), a heater 44 disposed between the insulating layers 36 and 38, and an electromagnetic shield 42 (also known as a ground plane layer) disposed between the insulating layers 34 and 36. A first inlet 94 is defined by a first surface of the insulating layer 24 and by a surface of the electrolyte 16, proximate the first reference electrode 14. Second sensing element 100 also includes a second inlet 95 that is defined by a first surface of the insulating layer 24 and by a surface of the electrolyte 16, proximate the second reference electrode 20. A third inlet 96 is defined by a first surface of the active layer 26 and a second surface of the insulating layer 24, proximate the electrode 80. A fourth inlet 98 is defined by a first surface of the active layer 26 and a second surface of the insulating layer 24, proximate the electrode 80. In addition, the sensing elements 10,100 include electrical leads 58, contact pads 60, 62, 70, 76, 90, 92, and may include additional ground plane layer(s) (not shown), and the like.

The first and second sensing electrodes 12, 18 are disposed in physical and ionic communication with electrolyte 16 and can be disposed in fluid communication with a sample gas (e.g., a gas being monitored or tested for its $NO_X$ concentration). Referring to FIGS. 1 and 2, this physical and ionic communication between electrolyte 16 and first and second electrodes 12,18 may be effected by forming insulating layer 22 with openings corresponding to and located under first and second electrodes 12,18, which extend through insulating layer 22, thereby allowing the sensor electrode material disposed on the top surface of insulating layer 22 to extend through the opening and provide physical and ionic communication with an upper surface of electrolyte 16. In one embodiment, the sensor electrode material may be screen printed onto an assembly of the insulating layer 22 and electrolyte 16 and fired such that it extends through the opening and makes the necessary physical and ionic communication with electrolyte 16. The electrode materials have $NO_X$ sensing capability (e.g., catalyzing $NO_X$ gas to produce an emf), electrical conducting capability (conducting electrical current produced by the emf), and gas diffusion capability (providing sufficient open porosity so that gas can diffuse throughout the electrode and to the interface region of the electrodes 12, 18 and electrolyte 16).

The first and second sensing electrodes 12, 18 are made from a barium iron oxide with the above properties at the selected operating temperatures. In an exemplary embodiment, the composition of the barium iron oxide is $BaFe_{12}O_{19}$. The $NO_X$ sensing capability of barium iron oxide having the composition $BaFe_{12}O_{19}$ may be enhanced by the addition of doping elements or dopants into the crystal lattice of the oxide as a substitute for barium, iron, or both. Thus, the barium iron oxide may be described as having the general composition $Ba_{(1-X)}A_XFe_{(12-Y)}B_YO_{19}$, where constituent A and constituent B are doping elements. Without limiting the foregoing, it is believed that the doping elements that are used as constituent A are substituted into the crystal lattice of the barium iron oxide composition described above in place of barium, and that doping elements that are used as constituent B are substituted in place of iron. Constituent A and constituent B elements may be substituted independently or in combination. Constituent A dopants are selected from the group consisting of Bi, La and Pb. The value of X is selected such that X is a real number where $0 \leq X < 1$. Constituent B dopants are selected from the group consisting of Al, B, Bi, Ca, Co, Cr, Cu, Er, Ga, In, Mg, Mn, Ni, Nb, Pb, Rh, Si, Sr, Ti, Ta, Zn and Zr. The value of Y is selected such that Y is a real number where $0 \leq Y < 12$.

Elements with valence lower than +3 substituted for Fe in $BaFe_{12}O_{19}$ can lower the contact impedance between the sensing electrodes 12,18 and the solid electrolyte 16 (such as yttria doped zirconia). More particularly, +2 and +1 valence elements may be used, including Co, Cu, Mg, Ni or Zn. The may be used in any suitable amount, and more particularly may be used in amounts of $0 \leq Y \leq 2$ in the formula described above.

Some dopants substituted for Fe in $BaFe_{12}O_{19}$ can enhance the NO sensing sensitivity, producing a higher emf output. These include Al, B, Cr, Ga, In, Mn, Nb, Si, Ti or Zr. Among these elements, Al, In and Ga are very effective, producing a large output emf in the presence of NO and a fast response time. They may be used in any suitable amount, and more particularly may be used in amounts of $0 \leq Y > 2$ in the formula described above.

Some dopants substituted for Fe in $BaFe_{12}O_{19}$ can enhance the $NO_2$ sensing sensitivity, producing a higher emf output. These include B, Ca, Co, Mg, Ni, Sr, or Zn. They may be used in any suitable amount, and more particularly may be used in amounts of $0 \leq Y \leq 2$ in the formula described above.

Some dopants substituted for Ba in $BaFe_{12}O_{19}$ can enhance the NO sensing sensitivity (with higher emf output) while depressing the $NO_2$ sensing sensitivity. One such element is Bi. They may be used in any suitable amount, and more particularly may be used in amounts of $0 \leq X \leq 0.2$ in the formula described above.

Some dopants substituted Fe in $BaFe_{12}O_{19}$ can enhance the response time of NOX sensors that employ these materials. They are Al, Bi, Co, Ga, In, Mg, Ni, Ta or Zr. Among these elements, Al, In and Ga are very effective in enhancing the response time. They may be used in any suitable amount, and more particularly may be used in amounts of $0 \leq Y < 2$ in the formula described above.

NO sensing sensitivity can be depressed such that most of the emf output results from $NO_2$ sensing sensibility. This can be achieved by doping the $BaFe_{12}O_{19}$ lattice on the Fe sites with B, Ca, Co, Ga, Er, Mg, Rh, Sr, or Zn, or on the Ba sites with La or Pb. Examples include $BaFe_{11.5}Ca_{0.5}O_{19}$, $BaFe_{11.5}In_{0.25}Co_{0.25}O_{19}$, $BaFe_{11.5}Ga_{0.25}Co_{0.25}O_{19}$, $BaFe_{11.5}Zn_{0.5}O_{19}$, $Ba_{0.99}Pb_{0.01}Fe_{12}O_{19}$, $BaFe_{11.9}Rh_{0.1}O_{19}$, $BaFe_{11.5}B_{0.5}O_{19}$, $BaFe_{11.5}Er_{0.5}O_{19}$, $BaFe_{11.75}Mg_{0.25}O_{19}$, $BaFe_{11.5}Sr_{0.50}O_{19}$, $BaFe_{11.8}Mg_{0.15}B_{0.05}O_{19}$ and $BaFe_{11.8}Mg_{0.15}Pb_{0.05}O_{19}$.

The $NO_X$ sensor material may also include a non-stoichiometric excess of Ba dispersed within the sensor material as a sintering aid. This may include an excess of up to about 5 atom percent of Ba.

As noted, the $NO_X$ sensing capability of barium iron oxide having the composition $BaFe_{12}O_{19}$ may also be enhanced by the addition of a plurality doping elements or dopants into the crystal lattice of the oxide as a substitute for barium, iron, or both. Additionally, a plurality of doping elements may be substituted for Fe in a given composition, rather than use of a single iron substitute. This relationship may be simply described as having the general composition $Ba_{(1-X)}A_XFe_{(12-Y-Z)}B_YC_ZO_{19}$ where there are two Fe dopant elements, where constituent A is a substitute for Ba, and constituents B and C are Fe dopant elements, where $0 \leq X < 1$ and $Y+Z$ is a real number where $0 \leq Y+Z < 12$. This formulaic notation will be understood to also include compositions that have more than two dopant element constituents (i.e. a plurality of C constituents) substituting for Fe, and where Z is representative of the stoichiometric amount of each of the plurality of C constituents.

The $NO_X$ sensor electrode materials may be made by any suitable method. In an exemplary embodiment, the sensor electrode material may be made by mixing powders of metal oxide precursors having the desired constituent elements in amounts sufficient to provide the desired stoichiometric composition. Metal oxide precursors can be metal oxides, or any material comprising the metal that can oxidize under during processing of the powders to form the sensor electrode, such as by sintering of the metal oxide precursor powder mixture to form the $NO_X$ sensor electrode material. The metal oxide precursors are used in an amount depending on the desired final microstructure and composition of the $NO_X$ sensor electrode material, and can be easily determined by a person of ordinary skill in the art. The metal oxide precursors are mixed using any suitable method to produce an intimate homogeneous mixture, such as by milling, by using a mortar and pestle, or the like. After mixing, the metal oxide precursor powders are heated to a temperature and for a time sufficient to form the desired $NO_X$ sensor electrode material composition. The heating may be done in air, but it is believed that for some combinations, heating other atmospheres or in vacuum may be desirable. In an exemplary embodiment, the heating was done in air at a temperature of 1200° C. for 6 hours.

After the formation of the desired $NO_X$ sensor electrode material, it is disposed on the solid electrolyte 16 to form first $NO_X$ sensor cell 12/16/14 or first and second $NO_X$ sensor cells 12/16/14, 18/16/20), comprising sensor electrode 12. This can be effected using any suitable deposition application or other technique available to one with ordinary skill in the art including, but not limited to, spray coating, painting, dip coating, screen printing, laminating, and the like.

In one advantageous embodiment, disposing is effected by screen printing. In this embodiment, the $NO_X$ sensor electrode material can be made into an ink, which also refers to a paste or other fluid form suitable for screen printing, and disposed onto the insulating layer 22 in contact solid electrolyte 16.

The ink can further comprise a binder, a carrier, a wetting agent, and the like, and combinations comprising at least one of the foregoing. The binder can be any material capable of providing adhesion between the ink and the substrate. Non-limiting examples of binders include acrylic resin, acrylonitrile, styrene, poly(acrylic acid), poly(methacrylic acid), poly(methyl acrylate), poly(methyl methacrylate), and the like, as well as combinations comprising at least one of the foregoing binders. Carriers include any material suitable for imparting desired printing, drying, and rheological characteristics of the ink. Non-limiting examples of carriers include volatile solvents which can dissolve polymer resins such as butyl acetate. Non-limiting examples of wetting agents include ethanol, isopropyl alcohol, methanol, cetyl alcohol, calcium octoate, zinc octoate and the like, as well as combinations comprising at least one of the foregoing.

The different constituents of the ink can be present in different amounts depending on the nature of the materials, and the product, and can be readily determined by a person with ordinary skill in the art. In general, the binder can be present in about 1 to about 40 wt %, the carrier can be present in about 1 to about 40 wt %, the wetting agent can be present in about 1 to about 20 wt %, and the $NO_X$ sensor electrode material can be present in about 15 to about 98 wt %, based on the total weight of the ink.

Fugitive materials can also be used in the ink formulations to produce a desired porosity in the final $NO_X$ sensor electrode, that is, a sufficient porosity to enable the $NO_X$ to enter the $NO_X$ sensor electrode and reach triple points (points where the electrode, electrolyte, and $NO_X$ meet to enable the desired reactions). Fugitive materials are materials that degrade leaving voids upon firing. Some non-limiting examples of fugitive materials include graphite, carbon black, starch, nylon, polystyrene, latex, other soluble organics (e.g., sugars and the like), and the like, as well as combinations comprising one or more of the foregoing fugitive materials. The fugitive material can be present in an amount of about 0.1 to about 20 wt %, based on the total weight of the ink.

The reference electrodes 14, 20 are disposed in physical contact and in ionic communication with the electrolyte 16, and can be disposed in fluid communication with the sample gas or reference gas; preferably with the sample gas. The reference electrodes materials have oxygen catalyzing capability (e.g., catalyzing equilibrium $O_2$ gas to produce an emf), electrical conducting capability (conducting electrical current produced by the emf), and/or gas diffusion capability (providing sufficient open porosity so that gas can diffuse throughout the electrode and to the interface region of the reference electrodes 14, 20 and electrolyte 22). Possible electrode materials include platinum (Pt), palladium (Pd), osmium (Os), rhodium (Rh), iridium (Ir), gold (Au), ruthenium (Ru), and the like, as well as mixtures or alloys comprising at least one of the foregoing materials. The electrode can include metal oxides such as zirconia and alumina that can increase the electrode porosity and increase the contact area between the electrode and the electrolyte. With respect to the size and geometry of the reference electrodes 14,20, it is generally adequate to provide current output sufficient to effect a reasonable signal resolution over a wide range of $NO_X$ concentrations. Generally, a thickness of about 1 to about 25 µm can be employed, more specifically a thickness of about 5 to about 20 µm, and even more specifically a thickness of about 10 to about 18 µm. The reference electrodes 14,20 can be formed using any suitable technique such as chemical vapor deposition, screen printing, sputtering, and stenciling, among others, in any combination, with screen printing of inks or pastes that include the electrode material onto appropriate tapes being advantageous due to simplicity, economy, and compatibility with the subsequent firing process. For example, reference electrode 14 can be screen printed onto an abutting layer 24 or the underside of the solid electrolyte. Further, the reference electrodes 14,20 can be embedded within either of the above layers.

The electrolyte layer 16 has oxygen ion conducting and fluid separation (limiting fluid communication of the sample gases on each side of the electrolyte layer 16) capabilities. The electrolyte layer 16 can be any size capable of providing sufficient ionic communication for the $NO_X$ sensing cell (12/16/20) or cells (12/16/20 and 18/16/20). The electrolyte layer 16 can be the entire length and width of the sensing element 10 or portions thereof. Any suitable electrolyte layer material having these characteristics may be used. Possible electrolyte layer materials include zirconium oxide (zirconia), cerium oxide (ceria), calcium oxide, yttrium oxide (yttria), lanthanum oxide, magnesium oxide, alumina oxide (alumina), indium oxide and the like, as well as combinations comprising at least one of the foregoing electrolyte materials, such as yttria doped zirconia, $LaGaO_3$, $SrCeO_3$, $BaCeO_3$, and $CaZrO_3$. These electrolyte materials may also include various dopants, alloying additions or other modifiers used to promote, prevent, stabilize or otherwise produce a desired microstructural affect, such as, for example, zirconia which is stabilized with respect to, among others, polymorphism, high temperature phase transformation, and the like, by the addition of calcium, barium, yttrium, magnesium, aluminum, lanthanum, cesium, gadolinium, ytterbium, scandium, or the like, or oxides thereof. The solid electrolyte layer 16 can be formed using any method available to one with ordinary skill in the art including, but not limited to, doctor blade slurry casting, tape casting, die pressing, roll compaction, stenciling, screen printing, and the like.

The air-fuel sensing cell (80/26/82) can detect the air to fuel ratio of the sample gas. When a constant potential is applied to electrodes 80 and 82, the current through the air-fuel sensing cell 80/26/82 is limited by the oxygen available in the inlets 96, or 98 and at the electrodes 80, 82. Therefore, by measuring the limiting current at the air-fuel sensing cell 80/26/82, the processor can determine the air-to-fuel ratio of the gas. This same cell can also be used for sensing the temperature of the gas. In this mode an AC signal will be applied to the electrode 80 and 82, and the impedance of the electrolyte 26 between the two electrodes 80 and 82 is used for temperature determination.

The heater 44 can be employed to maintain the sensing elements 10,100 at a selected operating temperature. The heater 44 can be positioned as part of the monolithic design of the sensing elements 10,100, for example between insulating layer 36 and insulating layer 38, in thermal communication with the air-fuel sensing cell 80/26/82 and the sensing cells 12/16/14, 18/16/20. In other embodiments, the heater could be in thermal communication with the cells without necessarily being part of a monolithic laminate structure with them, e.g., simply by being in close physical proximity to a cell. More specifically, the heater can be capable of maintaining the sensing end 21 of the sensing element 10 at a sufficient temperature to facilitate the various electrochemical reactions therein. The heater can be a resistance heater and can comprise a line pattern (connected parallel lines, serpentine, and/or the like (not shown)). The heater can comprise, for example, platinum, aluminum, palladium, and the like, as well as combinations comprising at least one of the foregoing, oxides comprising at least one of the foregoing metals. Contact pads, for example, the fourth contact pad 90 and the fifth contact pad 92, can transfer current to the heater from an external power source.

The temperature sensor (not shown) comprises any temperature sensor capable of monitoring the temperature of the sensing end 21 of the sensing elements 10,100, such as, for example, an impedance-measuring device or a metal-like resistance-measuring device. The metal-like resistance temperature sensor can comprise, for example, a line pattern (connected parallel lines, serpentine, and/or the like). Some possible materials include, but are not limited to, electrically conductive materials such as metals including platinum (Pt), copper (Cu), silver (Ag), palladium (Pd), gold (Au), tungsten (W), as well as combinations comprising at least one of the foregoing.

Disposed between the insulating layers 34 and 36 can be an electromagnetic shield 42. The electromagnetic shield 42 isolates electrical influences by dispersing electrical interferences and creating a barrier between a high power source (such as the heater) and a low power source (such as the temperature sensor and the gas sensing cell). The shield can comprise, for example, a line pattern (connected parallel lines, serpentine, cross hatch pattern, and/or the like). Any suitable electrically conductive material may be used. Some possible materials for the shield can include, without limitation, those materials discussed above for the heater or temperature sensor.

At the sensing end 21 of the sensing elements 10,100, the electrical leads 58, are disposed in physical contact and in electrical communication with electrodes 12, 14, 18, 20, 80, 82. In an exemplary embodiment, electrodes 80 and 82 and their associated electrical leads are disposed on an upper and a lower surface of electrolyte 26. Further, electrical leads 58 are disposed in electrical communication with the heater 44 and the electromagnetic shield 42. Each electrical lead extends from a contact pad or via toward the sensing end 21. Electrical leads not disposed on a top surface or a bottom surface of the sensing elements 10,100 are in electrical communication with the contact pads through vias formed in the layers. Two sets of three contact pads are disposed at the terminal end 81 of the sensing element 10: the first, second, and third contact pads 60, 70, 76, respectively, are disposed on the upper surface of the sensing element 10, and the fourth, fifth and sixth contact pads 62, 90, 92, respectively, are disposed on the lower surface of the sensing element 10. The first, second, third, and fourth contact pads 60, 62 70, 76 are in electrical communication with a controller (not shown), and the fifth and sixth contact pads 90, 92 are in electrical communication with an external power source (not shown) which may also be incorporated into or associated with a controller or controllers, including various microprocessor-based controllers.

The insulating layers 22, 24, 28, 34, 36, 38 can comprise a dielectric material such as alumina (i.e., aluminum oxide ($Al_2O_3$)), other insulating ceramics, and the like. Each of the insulating layers can comprise a sufficient thickness to attain the desired insulating and/or structural properties. For example, each insulating layer can have a thickness of about 1 up to about 200 micrometers or so, depending upon the number of layers employed, or, more specifically, a thickness of about 50 micrometers to about 200 micrometers. Further, the sensor element 10 can comprise additional insulating layers to isolate electrical devices, segregate gases, and/or to provide additional structural support.

The active layers 26, 30, and 32 can include material that, while under the operating conditions of sensing element 10,100, is capable of permitting the electrochemical transfer of oxygen ions. These include the same or similar materials to those described as comprising electrolyte layer 16. Each of the active layers can comprise a thickness of up to about 200 micrometers or so, depending upon the number of layers employed, or, more specifically, a thickness of about 50 micrometers to about 200 micrometers.

Figure 3:
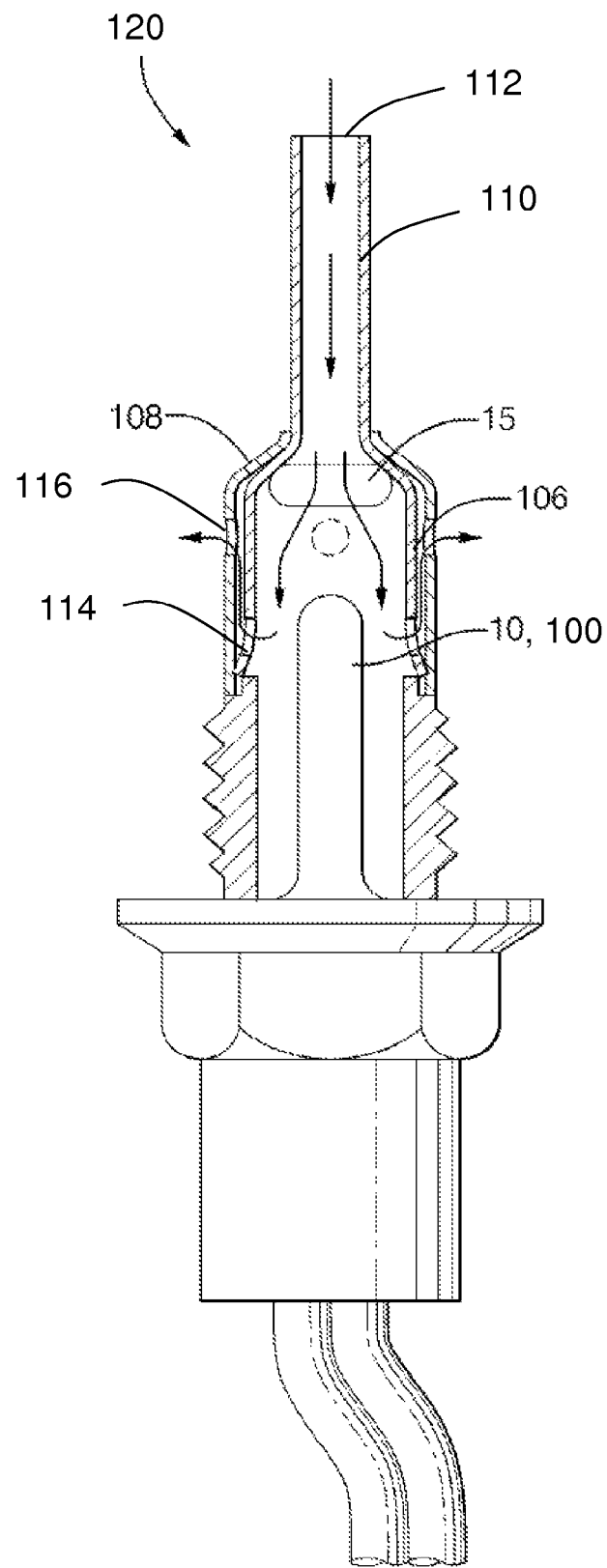
FIG. 3 is a cross-sectional view of an exemplary embodiment of a gas sensor that includes a sensor element, as described herein.

Referring to FIG. 3, for placement in a gas stream, gas sensor element 10 can be disposed within a protective casing 120. The protective casing 120 can comprise an outer shield 108 having a plurality of outer shield holes 116. An inner shield 106 has a plurality of passages 114, which allows fluid to enter a space between the inner shield 106 and the outer shield 108. Outer shield holes 116 allow fluid in the space between inner shield 106 and outer shield 108 to exit the casing 120. An optional sampling tube 110 having an inlet 112 extends from the outer shield 108. The sampling tube opens into a catalyst surrounding sensing element 10,100. Arrows are shown to illustrate the general fluid flow direction within the protective casing.

The plurality of exhaust passages 114 may be disposed through inner shield 106 to allow the exhaust fluid a sufficient time to contact the sensing element 10,100 prior to exiting the protective casing 120. The plurality of exhaust passages 114 can be any size or shape sufficient to allow the passage of exhaust fluid.

Suitable materials for the protective casing 120 can include materials that are capable of resisting under-car salt and other contaminants, operating temperatures, and corrosion. For example, ferrous materials are employed including various stainless steels, such as ferritic stainless steels. Ferritic stainless steels may include stainless steels such as, e.g., SS-409, SS-316, and the like.

A catalyst 15 can be disposed in the exhaust stream, upstream from the first sensing cell 12/16/14. The catalyst 15 can comprise material(s) capable of converting hydrocarbons, carbon monoxide, ammonia, and/or hydrogen into water, nitrogen, and/or carbon dioxide. In one embodiment, the catalyst 15 includes a material that, under the operating conditions of sensing element 10,100, is capable of efficiently converting NO to $NO_2$. In a second embodiment, the catalyst 15 includes a material that, under the operating conditions of the sensing element 10,100 is capable of converting $NO_2$ to NO. The catalyst 15 can comprise materials including platinum, platinum alloys, and the like, as well as combinations comprising at least one of the foregoing. The catalyst 15 can further comprise zeolite(s) (e.g., alumina-silica zeolite powder).

The catalyst 15 can be disposed proximate various locations in the casing 120. In general, the catalyst 15 can be disposed at a location in which the sample gas can sufficiently contact the catalyst 15 upstream from the sensing element 10,100. For example the catalyst 15 can be disposed proximate the sampling tube 110 or can be disposed proximate the inner surface of the inner shield 106. The catalyst 15 can also be disposed outside the casing 120 upstream from the sensing element 10,100. For example, the catalyst 15 could be part of a catalyst bed reactor, upstream from the inlet 112 of the casing 120. In an exemplary embodiment, the sensing element 10,100 is disposed in an exhaust stream in fluid communication with engine exhaust. In addition to $NH_3$, $O_2$, and $NO_X$, the sensor's operating environment includes other combustion by-products, for example, hydrocarbons, hydrogen, carbon monoxide, water, sulfur, sulfur-containing compounds, and/or combustion radicals (such as hydrogen and hydroxyl ions), and the like.

The sensing element 10,100 can be formed using any suitable method, including various ceramic processing techniques. For example, milling processes (e.g., wet and dry milling processes including ball milling, attrition milling, vibration milling, jet milling, and the like) can be used to size ceramic powders into desired particle sizes and desired particle size distributions to obtain physical, chemical, and electrochemical properties. The ceramic powders can be mixed with plastic binders to form various shapes. For example, the structural components (e.g., insulating layers 22, 24, 28, 34, 36, and 38 and the active or electrolyte layers 16, 26, 30, 32) can be formed into "green" tapes by tape-casting, role-compacting, or similar processes. The non-structural components (e.g., the first electrode 12, the second electrode 18, the reference electrodes 14, 20, the electrical leads, and the contact pads) can be formed into a tape or can be deposited onto the structural components by any suitable method, including various ceramic processing techniques (e.g., sputtering, painting, chemical vapor deposition, screen-printing, stenciling, and the like).

The inlets 94, 95, 96, 98, can be formed either by disposing fugitive material (material that will dissipate during the sintering process, e.g., graphite, carbon black, starch, nylon, polystyrene, latex, other insoluble organics, as well as compositions comprising one or more of the foregoing fugitive materials) or by disposing material that will leave sufficient open porosity in the fired ceramic body to allow gas diffusion therethrough. Once the "green" sensor is formed, the sensor can be sintered at a selected firing cycle to allow controlled burn-off of the binders and other organic materials and to form the ceramic material of the sensor with the desired physical, microstructural, compositional and other properties described herein.

The first $NO_X$ sensing cell 12/16/14 and the second $NO_X$ sensing cell 18/16/20 can generate an emf as described by the Nernst Equation, particularly as adapted for use under non-equilibrium conditions. In the exemplary embodiment, the sample gas is introduced to the sensing electrode(s) and is diffused throughout the porous electrode materials. In the sensing electrode(s), catalytic materials induce catalytic reactions in the sample gas. These reactions include catalyzing $NO_2$ to form NO and $H_2O$ and catalyzing NO and $O^{-2}$ to form $NO_2$. Similarly, in the reference electrode 14, 20, catalytic material induces catalytic reactions in the reference gas, converting equilibrium oxygen gas ($O_2$) to oxide ions ($O^{-2}$) or vice versa, and thereby producing an emf. Therefore, the electrical potential difference between any the sensing electrode(s) 12, 18, and the corresponding reference electrode(s) 14, 20 can be measured to determine an emf.

The primary reactants at electrodes of the first $NO_X$ sensing cell 12/16/14 and second $NO_X$ sensing cell 18/16/20 are NO, $H_2O$, $NO_2$ and $O_2$. The partial pressure of reactive components at the electrodes of the $NO_X$ sensing cell(s) can be determined from the cell's electromotive force (emf) by using the non-equilibrium Nernst Equation (1):

$$EMF \approx \frac{kT}{2e}Ln(P_{NO}) - \frac{kT}{4e}Ln(P_{O_2}) - \frac{kT}{2e}Ln(P_{H_2O}) - \frac{kT}{2e}Ln(P_{NO_2}) + \text{constant} \quad (1)$$

where: k=the Boltzmann constant
T=the absolute temperature of the gas
e=the electron charge unit
a, b, c, d are constants
Ln=natural log
$P_{NH_3}$=the partial pressure of ammonia in the gas,
$P_{O_2}$=the partial pressure of oxygen in the gas,
$P_{NO_2}$=the partial pressure of nitrogen dioxide in the gas,
$P_{H_2O}$=the partial pressure of water vapor in the gas
$P_{NO}$=the partial pressure of nitrogen monoxide in the gas.

The temperature sensor can measure a temperature indicative of the absolute gas temperature (T). The oxygen and water vapor content, e.g., partial pressures, in the unknown gas can be determined from the air-fuel ratio as measured by the air-fuel sensing cell 80/26/82.

In a first embodiment, the sample gas contacts the catalyst 15. The catalyst 15 catalyzes NO to $NO_2$ so that $NO_X$ in the sample gas exists in the form $NO_2$. The heater heats the $NO_X$ sensing cell 12/16/14 to a selected operating temperature (e.g., 200° C. to 400° C.), where the electrode 12 will sense $NO_2$. The $NO_X$ sensing cell 12/16/14 generates an emf based on the $NO_2$ concentration, which is indicative of the total $NO_X$ concentration of the sample gas prior to the sample gas contacting the catalyst 15. When the NO concentration is relatively low in comparison to the $NO_2$ concentration, the term $kT/2e\ Ln(P_{NO})$ can be eliminated from the equation, and the partial pressure of $NO_2$ becomes the only unknown in Equation (1). Therefore, the controller can apply Equation (1) (or a suitable approximation thereof) to determine the amount of $NO_2$, or the processor can access a lookup table from which the NO partial pressure can be selected in accordance with the emf output from the NO sensing cell 12/16/14 and from the air fuel sensing cell 80/26/82.

In a second embodiment, the sample gas can optionally contact the catalyst 15. The catalyst 15 catalyzes $NO_2$ to NO so that $NO_X$ in the sample gas exists in the form NO. The heater heats the $NO_X$ sensing cell 12/16/14 to a selected operating temperature (e.g., about 650° C. to about 750° C.), where the electrode 12 will sense NO. The $NO_X$ sensing cell 12/16/14 generates an electromotive force based on the NO concentration, which is indicative of the total $NO_X$ concentration of the sample prior to the sample gas contacting the catalyst 15. When the $NO_2$ concentration is relatively low when compared with the NO concentration, the term $$\frac{kT}{2e}\text{Ln}(P_{NO_2})$$

can be eliminated from the Equation, and the partial pressure of NO becomes the only unknown in Equation (1). Therefore, the processor can apply Equation (1) (or a suitable approximation thereof) to determine the amount of NO, or the processor can access a lookup table from which the NO partial pressure can be selected in accordance with the electromotive force output from the $NO_X$ sensing cell 12/16/14 and from the air fuel sensing cell 80/26/82.

In a third embodiment, the heater heats the sensor producing a thermal gradient across the sensing element 10,100 (see FIG. 2). By disposing the heater adjacent the first sensing cell 12/16/14, the heater can heat the first sensing cell 12/16/14 to a first selected operating temperature (e.g., about 700° C. to about 800° C.) wherein the electrode 12 will sense NO but not $NO_2$. The second sensing cell 18/16/20 can operate at a second selected operating temperature (e.g., 500° C. to about 650° C.). The second sensing cell reacts with both $NO_2$ and NO, producing an emf. By using the emf from the first sensing cell and the second sensing cell, the processor can access a lookup table from which the $NO_2$ and NO partial pressure can be selected in accordance with the electromotive force output from the $NO_X$ sensing cell 12/16/14 and from the air fuel sensing cell 18/16/20. The NO partial pressure can also be determined by Equation (1) or a suitable approximation thereof. In this embodiment, the controller can determine both the concentration of NO and the concentration of $NO_2$ in the sample gas.

The air to fuel ratio can be obtained by a controller, such as an engine control module (ECM) as described, for example in GB2347219A, or by having an air to fuel ratio sensor integrated into the sensor 10. Alternatively, a complete mapping of $H_2O$ and $O_2$ concentrations under all engine running conditions (measured by instruments such as mass spectrometer) can be obtained empirically and stored in ECM in a look-up table with which the sensor is in signal communication. Once the oxygen and water vapor content information is known, the controller can use the information to more accurately determine the partial pressures of the sample gas components. Typically, the water and oxygen correction according to Equation (1) is a small number within the water and oxygen ranges of diesel engine exhaust. This is especially true when the water is in the range of 1.5 weight percent (wt %) to 10 wt % in the engine exhaust. This is because the water and oxygen have opposite sense of increasing or decreasing at any given air to fuel ratio and both effects cancel each other in Equation (1). Where there is no great demand for sensing accuracy (such as ±0.1 part per million by volume (ppm)), the water and oxygen correction in Equation 1 is unnecessary.

The advantageous performance of the $NO_X$ sensor electrode materials described herein and their applicability to gas sensor elements and gas sensors which include NOX sensing capability is illustrated by the examples provided below, which also include comparative examples of the performance of related art $NO_X$ sensor electrode materials.

EXAMPLE 1

Figure 4:
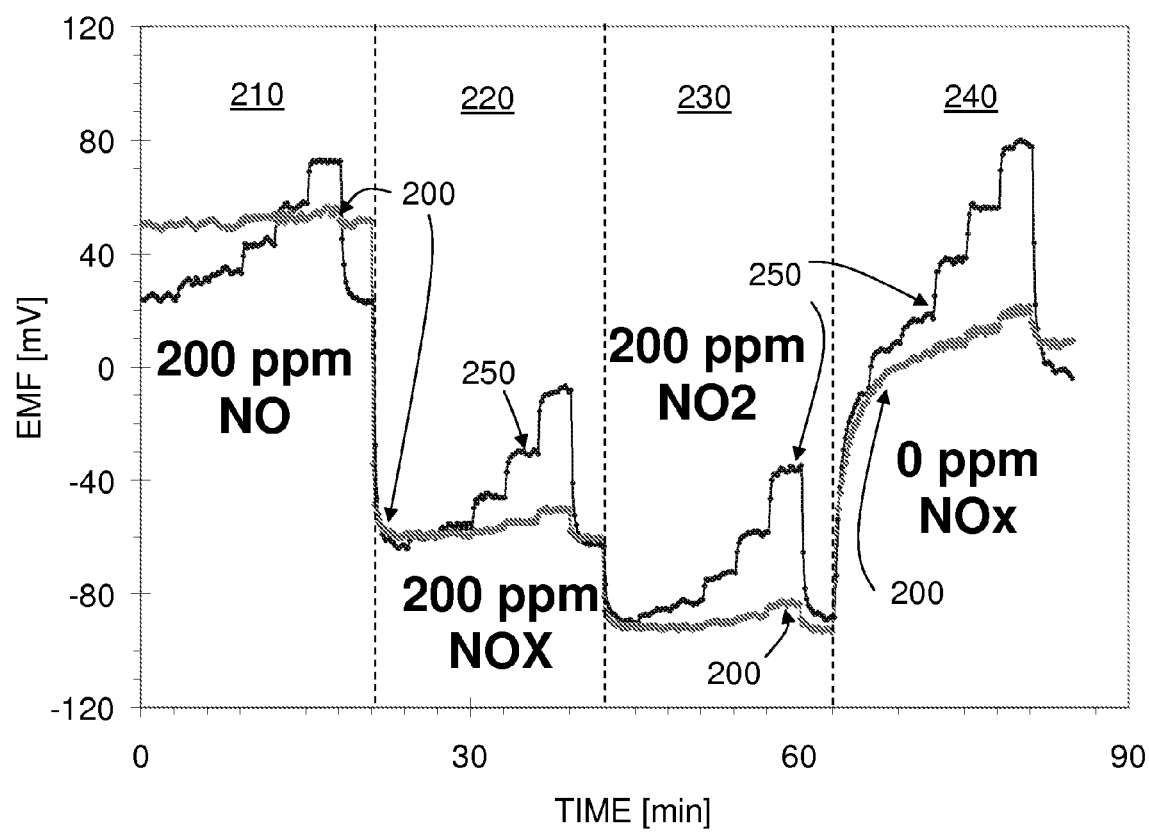
FIG. 4 is a graphical representation of emf output as a function of $NOX/NH_3$ gas concentration for the $NO_X$ sensor cell of Example 1.

The composition of the sensor material in this example was $BaFe_{11.95}B_{0.05}O_{19}$. It is made of $BaCO_3$, $Fe_2O_3$, $B_2O_3$ oxides, mechanically mixed and fired at 1200° C. for 6 hours in air to produce a powder of an oxide having the chemical composition indicated above. The oxide was formulated into a thick film ink as described herein, printed onto the surface of an electrolyte layer as described herein and assembled into a sensor element as described herein. The sensor element was fabricated into a $NO_X$ sensor as described herein. The $NO_X$ sensor was used to make emf measurements of several known $NO_X$ and $NH_3$ mixtures in order to evaluate the performance of the sensor elements and, more particularly, the performance of the oxide material described above as a $NO_X$ sensor material and its sensitivity to $NH_3$. The results are illustrated in plot 200 of FIG. 4, where the emf output of the sensors for various gas compositions are illustrated with respect to four different zones on the chart. The first zone 210 corresponds to exposure of the sensor to 200 PPM of NO gas with varying $NH_3$ concentrations of 0, 5, 10, 25, 50, 100 and 0 PPM in a carrier gas. The second zone 220 corresponds to exposure of the sensor to 100/100 PPM of $NO/NO_2$ gas with varying $NH_3$ concentrations of 0, 5, 10, 25, 50, 100 and 0 PPM in a carrier gas. The third zone 230 corresponds to exposure of the sensor to 200 PPM $NO_2$ gas with varying $NH_3$ concentrations of 0, 5, 10, 25, 50, 100 and 0 PPM in a carrier gas. The fourth zone 240 corresponds to exposure of the sensor to $NO_X$ gas with varying $NH_3$ concentrations of 0, 5, 10, 25, 50, 100 and 0 PPM in a carrier gas. The carrier gas was 10.5% volume percent $H_2O$ balanced with 1.5% volume percent $N_2$. Referring again to FIG. 4, plot 250 is a comparative example of a sensor electrode material of $TbCrO_3$. As may be seen, plot 250 illustrates the susceptibility of a sensor of having a sensor electrode of $TbCrO_3$ as a sensor material to $NH_3$ cross interference. In contrast, the exemplary composition of the sensor material in this example, $BaFe_{11.95}B_{0.05}O_{19}$, showed very little susceptibility to cross-interference from $NH_3$, and is, therefore, a good electrode material for both NO and NO2 sensing, particularly where the sensor may also be exposed to $NH_3$.

EXAMPLE 2

Figure 5:
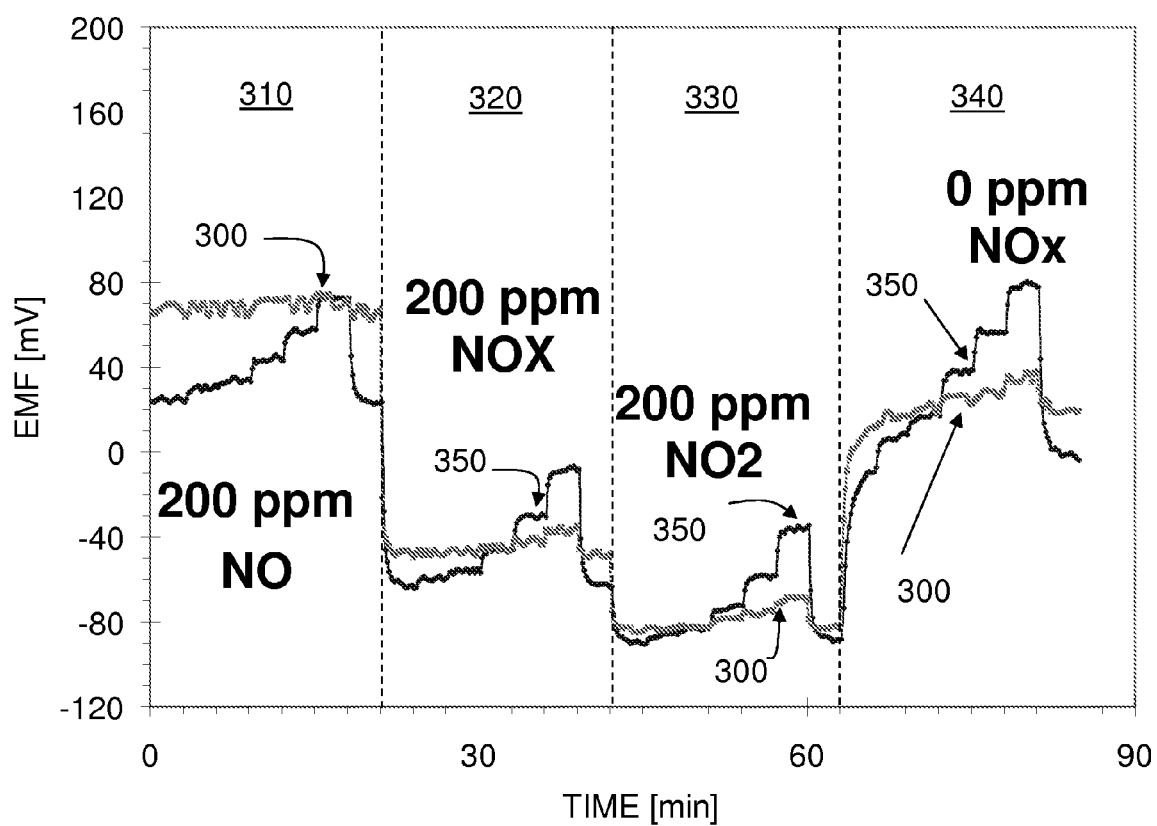
FIG. 5 is a graphical representation of emf output as a function of $NOX/NH_3$ gas concentration for the $NO_X$ sensor cell of Example 2.

The composition of the sensor material in this example was $BaFe_{11.75}In_{0.25}O_{19}$. It is made of $BaCO_3$, $Fe_2O_3$, $In_2O_3$ oxides, mechanically mixed and fired at 1200° C. for 6 hours in air to produce a powder of an oxide having the chemical composition indicated above. The oxide was formulated into a thick film ink as described herein, printed onto the surface of an electrolyte layer as described herein and assembled into a sensor element as described herein. The sensor element was fabricated into a $NO_X$ sensor as described herein. The $NO_X$ sensor was used to make emf measurements of several known $NO_X$ and $NH_3$ mixtures in order to evaluate the performance of the sensor elements and, more particularly, the performance of the oxide material described above as a $NO_X$ sensor material and its sensitivity to $NH_3$. The results are illustrated in plot 300 of FIG. 5, where the emf output of the sensors for various gas compositions are illustrated with respect to four different zones on the chart. The first zone 310 corresponds to exposure of the sensor to 200 PPM of NO gas with varying $NH_3$ concentrations of 0, 5, 10, 25, 50, 100 and 0 PPM in a carrier gas. The second zone 320 corresponds to exposure of the sensor to 100/100 PPM of $NO/NO_2$ gas with varying $NH_3$ concentrations of 0, 5, 10, 25, 50, 100 and 0 PPM in a carrier gas. The third zone 330 corresponds to exposure of the sensor to 200 PPM $NO_2$ gas with varying $NH_3$ concentrations of 0, 5, 10, 25, 50, 100 and 0 PPM in a carrier gas. The fourth zone 340 corresponds to exposure of the sensor to $NO_X$ gas with varying $NH_3$ concentrations of 0, 5, 10, 25, 50, 100 and 0 PPM in a carrier gas. The carrier gas was 10.5% volume percent $H_2O$ balanced with 1.5% volume percent $N_2$. Referring again to FIG. 4, plot 350 is a comparative example of a sensor electrode material of $TbCrO_3$. As may be seen, plot 350 illustrates the susceptibility of a sensor of having a sensor electrode of $TbCrO_3$ as a sensor material to $NH_3$ cross interference. In contrast, the exemplary composition of the sensor material in this example, $BaFe_{11.975}In_{0.025}O_{19}$, showed very little susceptibility to cross-interference from $NH_3$, and is, therefore, a good electrode material for both NO and NO2 sensing, particularly where the sensor may also be exposed to $NH_3$.

EXAMPLE 3

Figure 6:
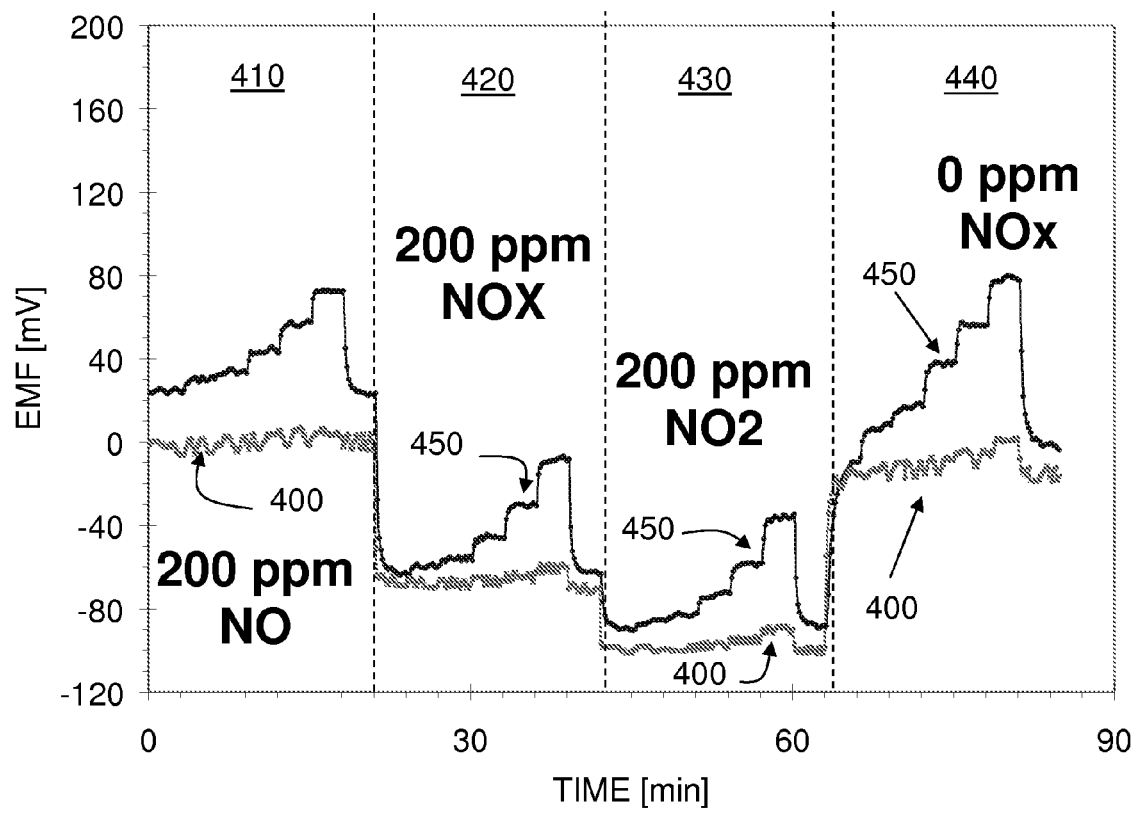
FIG. 6 is a graphical representation of emf output as a function of $NOX/NH_3$ gas concentration for the $NO_X$ sensor cell of Example 3.

The composition of the sensor material in this example was $BaFe_{11.5}Mg_{0.5}O_{19}$. It is made of $BaCO_3$, $Fe_2O_3$, MgO oxides, mechanically mixed and fired at 1200° C. for 6 hours in air to produce a powder of an oxide having the chemical composition indicated above. The oxide was formulated into a thick film ink as described herein, printed onto the surface of an electrolyte layer as described herein and assembled into a sensor element as described herein. The sensor element was fabricated into a $NO_X$ sensor as described herein. The $NO_X$ sensor was used to make emf measurements of several known $NO_X$ and $NH_3$ mixtures in order to evaluate the performance of the sensor elements and, more particularly, the performance of the oxide material described above as a $NO_X$ sensor material and its sensitivity to $NH_3$. The results are illustrated in plot 400 of FIG. 6, where the emf output of the sensors for various gas compositions are illustrated with respect to four different zones on the chart. The first zone 410 corresponds to exposure of the sensor to 200 PPM of NO gas with varying $NH_3$ concentrations of 0, 5, 10, 25, 50, 100 and 0 PPM in a carrier gas. The second zone 420 corresponds to exposure of the sensor to 100/100 PPM of $NO/NO_2$ gas with varying $NH_3$ concentrations of 0, 5, 10, 25, 50, 100 and 0 PPM in a carrier gas. The third zone 430 corresponds to exposure of the sensor to 200 PPM $NO_2$ gas with varying $NH_3$ concentrations of 0, 5, 10, 25, 50, 100 and 0 PPM in a carrier gas. The fourth zone 440 corresponds to exposure of the sensor to $NO_X$ gas with varying $NH_3$ concentrations of 0, 5, 10, 25, 50, 100 and 0 PPM in a carrier gas. The carrier gas was 10.5% volume percent $H_2O$ balanced with 1.5% volume percent $N_2$. Referring again to FIG. 6, plot 450 is a comparative example of a sensor electrode material of $TbCrO_3$. As may be seen, plot 450 illustrates the susceptibility of a sensor of having a sensor electrode of $TbCrO_3$ as a sensor material to $NH_3$ cross interference. In contrast, the exemplary composition of the sensor material in this example, $BaFe_{11.5}Mg_{0.5}O_{19}$, showed some susceptibility to cross-interference from $NH_3$ in the gas mixtures that included NO, but very little susceptibility to cross-interference from $NH_3$ with regard to $NO_2$, and is, therefore, a good electrode material for $NO_2$ sensing, particularly where the sensor may also be exposed to $NH_3$.

The sensor and methods described herein enable the determination of $NO_X$ concentration and, in some cases, composition. The sensor and methods can be used for on board diagnostics (OBD) or other control applications for vehicle exhaust treatment systems, such as diesel exhaust treatment systems, and including various systems designed to control or otherwise reduce the $NO_X$ components of vehicle emissions.

It should be noted that the terms "first," "second," and the like, herein do not denote any order, quantity, or importance, but rather are used to distinguish one element from another, and the terms "a" and "an" herein do not denote a limitation of quantity, but rather denote the presence of at least one of the referenced items. As used herein, "combination" is inclusive of blends, mixtures, alloys, reaction products, and the like, as appropriate. The modifier "about" used in connection with a quantity is inclusive of the stated value and has the meaning dictated by the context (e.g., includes the degree of error associated with measurement of the particular quantity). Furthermore, all ranges disclosed herein are inclusive and combinable (e.g., ranges of "up to about 25 weight percent (wt. %), with about 5 wt. % to about 20 wt. % desired, and about 10 wt. % to about 15 wt. % more desired," are inclusive of the endpoints and all intermediate values of the ranges, e.g., "about 5 wt. % to about 25 wt. %, about 5 wt. % to about 15 wt. %", etc.). Finally, unless defined otherwise, technical and scientific terms used herein have the same meaning as is commonly understood by one of skill in the art to which this invention belongs. The suffix "(s)" as used herein is intended to include both the singular and the plural of the term that it modifies, thereby including one or more of that term (e.g., the metal(s) includes one or more metals). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., it includes the degree of error associated with measurement of the particular quantity).

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A $NO_X$ sensor comprising a sensor material, said material comprising $Ba_{(1-X)}A_XFe_{(12-Y)}B_YO_{19}$, where constituent A and constituent B are doping elements; constituent A is selected from the group consisting of Bi, La and Pb; constituent B is selected from the group consisting of Al, B, Bi, Ca, Co, Cr, Cu, Er, Ga, In, Mg, Mn, Ni, Nb, Pb, Rh, Si, Sr, Ti, Ta, Zn and Zr; X is a real number where $0 \leq X < 1$ and Y is a real number where $0 \leq Y < 12$.

2. The $NO_X$ sensor of claim 1, wherein B is Co, Cu, Mg, Ni or Zn.

3. The $NO_X$ sensor of claim 2, wherein $0 \leq Y \leq 2$.

4. The $NO_X$ sensor of claim 1, wherein B is Al, B, Cr, Ga, In, Mn, Nb, Si, Ti or Zr.

5. The $NO_X$ sensor of claim 1, wherein B is Al, Ga or In and $0 \leq Y \leq 2$.

6. The $NO_X$ sensor of claim 1, wherein B is B, Ca, Co, Mg, Ni, Sr, or Zn.

7. The $NO_X$ sensor of claim 6, wherein $0 \leq Y \leq 2$.

8. The $NO_X$ sensor of claim 1, wherein B is Al, Bi, Co, Ga, In, Mg, Ni, Ta or Zr.

9. The $NO_X$ sensor of claim 1, wherein A is Bi.

10. The $NO_X$ sensor of claim 9, wherein $0 \leq X \leq 0.2$.

11. The $NO_X$ sensor of claim 1, wherein the sensor further comprises a sensor electrode in electrical contact with the sensor material.

12. The $NO_X$ sensor of claim 11, wherein the sensor electrode comprises Pt, Pd, Rh, Os, Ir, Ru or Au.

13. The $NO_X$ sensor of claim 1, wherein A is La or Pb or B is B, Ca, Co, Ga, Er, Mg, Rh, Sr, or Zn.

14. The $NO_X$ sensor of claim 13, wherein the sensor material comprises $BaFe_{11.5}Ca_{0.5}O_{19}$, $BaFe_{11.5}Zn_{0.5}O_{19}$, $Ba_{0.99}Pb_{0.01}Fe_{12}O_{19}$, $BaFe_{11.9}Rh_{0.1}O_{19}$, $BaFe_{11.5}B_{0.5}O_{19}$, $BaFe_{11.5}Er_{0.5}O_{19}$, $BaFe_{11.75}Mg_{0.25}O_{19}$ or $BaFe_{11.5}Sr_{0.5}O_{19}$.

15. The $NO_X$ sensor of claim 1, wherein the sensor material further comprises a non-stoichiometric excess of Ba dispersed within the sensor material as a sintering aid.

16. A $NO_X$ sensor comprising a sensor material, said material comprising $Ba_{(1-X)}A_XFe_{(12-Y-Z)}B_YC_ZO_{19}$, where constituent A, constituent B and constituent C are doping elements; constituent A is selected from the group consisting of Bi, La and Pb; constituents B and C are each selected from the group consisting of Al, B, Bi, Ca, Co, Cr, Cu, Er, Ga, In, Mg, Mn, Ni, Nb, Pb, Si, Rh, Sr, Ti, Ta, Zn and Zr; X is a real number where $0 \leq X < 1$ and Y+Z is a real number where $0 \leq Y+Z < 12$.

17. The $NO_X$ sensor of claim 16, wherein B and C are each selected from the group consisting of Co, Cu, Mg, Ni and Zn.

18. The $NO_X$ sensor of claim 16, wherein B and C are each selected from the group consisting of Al, B, Cr, Ga, In, Mn, Nb, Si, Ti and Zr.

19. The $NO_X$ sensor of claim 16, wherein B and C are each selected from the group consisting of B, Ca, Co, Mg, Ni, Sr, and Zn.

20. The $NO_X$ sensor of claim 16, wherein B and C are each selected from the group consisting of Al, Bi, Co, Ga, In, Mg, Ni, Ta and Zr.

21. The $NO_X$ sensor of claim 16, wherein A is Bi.

22. The $NO_X$ sensor of claim 16, wherein the sensor further comprises a sensor electrode in electrical contact with the sensor material.

23. The $NO_X$ sensor of claim 16, wherein A is La or Pb, or B is B, Ca, Co, Ga, Er, Mg, Rh, Sr, or Zn.

24. The $NO_X$ sensor of claim 23, wherein the sensor material comprises $BaFe_{11.5}In_{0.25}Co_{0.25}O_{19}$, $BaFe_{11.5}Ga_{0.25}Co_{0.25}O_{19}$, $BaFe_{11.8}Mg_{0.15}B_{0.05}O_{19}$ or $BaFe_{11.8}Mg_{0.15}Pb_{0.05}O_{19}$.

25. The $NO_X$ sensor of claim 16, wherein the sensor material further comprises a non-stoichiometric excess of Ba dispersed within the sensor material as a sintering aid.

* * * * *